United States Patent [19]

Peterson

[11] 4,395,913

[45] Aug. 2, 1983

[54] BROADBAND ELECTROMAGNETIC ACOUSTIC TRANSDUCERS

[75] Inventor: William E. Peterson, Thousand Oaks, Calif.

[73] Assignee: Rockwell International Corporation, El Segundo, Calif.

[21] Appl. No.: 288,961

[22] Filed: Jul. 31, 1981

[51] Int. Cl.$^3$ ............................................. G01N 29/04
[52] U.S. Cl. ................................ 73/643; 310/313 A; 343/17.2 PC
[58] Field of Search ................... 73/643; 324/237, 238; 310/313 R, 313 A, 313 B; 343/17.2 PC

[56] References Cited

U.S. PATENT DOCUMENTS

| | | | |
|---|---|---|---|
| 3,845,419 | 10/1974 | Nudd | 310/313 B |
| 3,850,028 | 11/1974 | Thompson et al. | |
| 4,058,002 | 11/1977 | Moran | 73/643 |
| 4,127,035 | 11/1978 | Vasile | 73/643 |
| 4,218,924 | 8/1980 | Fortunko et al. | |
| 4,232,557 | 11/1980 | Vasile | 73/643 |
| 4,295,214 | 10/1981 | Thompson | |
| 4,312,231 | 1/1982 | Kawashima et al. | 73/643 |

OTHER PUBLICATIONS

Isbell, Log Periodic Dipole Arrays, IRE Transactions on Antennas and Propagation, May 1960, p. 260.

Primary Examiner—Howard A. Birmiel
Attorney, Agent, or Firm—H. Fredrick Hamann; Craig O. Malin; John J. Deinken

[57] ABSTRACT

A broadband electromagnetic acoustic transducer is disclosed for use with an electrically conductive object. The transducer includes a source of magnetic flux for establishing a static magnetic field in the object and an electrical conductor for inducing eddy currents in the object when an alternating current is applied to the conductor. The magnetic field and the conductor are oriented so that the vector product of the magnetic field and the eddy currents produces an instantaneous force field in the object which is periodically alternately directed with a logarithmic periodicity. The source of magnetic flux may be provided by a plurality of alternately oriented magnets aligned along a propagation direction. Alternatively, the conductor may be a serpentine conductor with a plurality of parallel elements which are perpendicular to a propagation direction, the ratio of adjacent spacings between the elements being constant.

17 Claims, 6 Drawing Figures

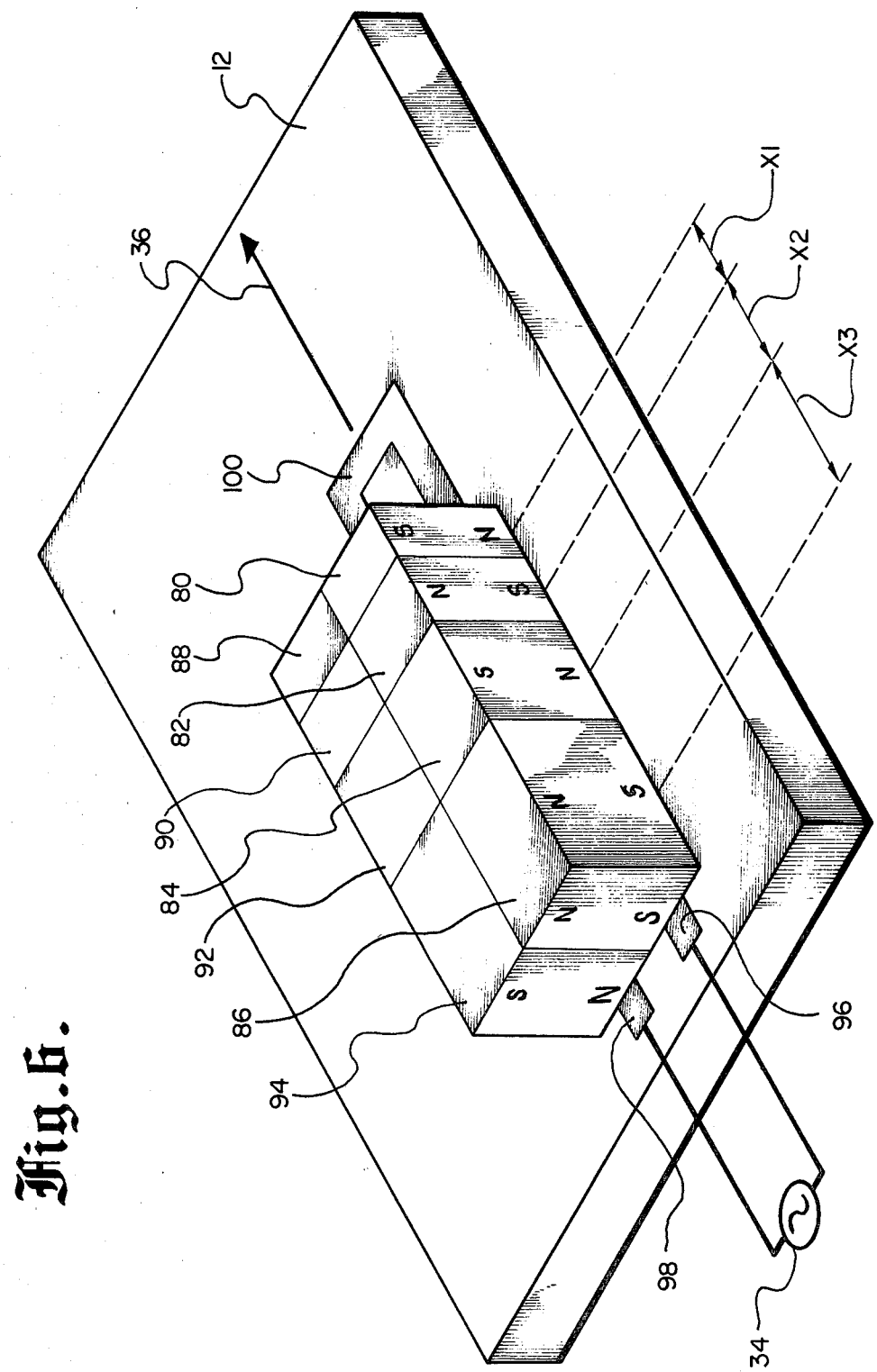

BROADBAND ELECTROMAGNETIC ACOUSTIC TRANSDUCERS

BACKGROUND OF THE INVENTION

This invention relates to techniques for generating and detecting ultrasonic waves and, more particularly, to electromagnetic acoustic transducers.

An increasing emphasis on efficiency and economy in many areas of modern structural design has stimulated a more widespread use of the techniques of nondestructive testing. Nondestructive methods are important because of their ability to locate a structural defect at an early stage in the life of a flaw, permitting the appropriate corrective action, such as removing and replacing the defective component, to be initiated before the defect causes a catastrophic failure.

Before nondestructive testing methods became available, it was necessary to design structural components under the assumption that flaws of a certain size would be found in the construction materials. This assumption led to specifying components of sufficient size and strength to function properly even when the assumed defects were present. When nondestructive testing measures are implemented, however, such structural components may be manufactured and assembled more economically by reducing dimensions and substituting less expensive materials. Nondestructive inspection techniques can thus be utilized to maintain a desired level of reliability in a physical structure while reducing construction and material costs.

One of the many types of nondestructive testing techniques is ultrasonics, in which the interaction between acoustic wave energy and the internal structure of an object is analyzed to predict the physical integrity of the object. A key element in any ultrasonic nondestructive testing system is the transducer, which is used to convert electrical energy into acoustic wave energy and vice versa. Traditionally, the high conversion efficiency and modest cost of piezoelectric materials have led to their widespread use as ultrasonic transducers in many applications. Piezoelectric transducers are hampered, however, by the need to be coupled to the ultrasonic medium by a liquid or solid bond.

The ability to operate at high speeds and elevated temperatures, in remote locations, with broadband and reproducible acoustic coupling, and without the need for subsequent clean up operations of a liquid bond have spurred the development of noncontact techniques, such as electrostatic transducers, optical techniques, and electromagnetic transducers, which have supplanted piezoelectric transducers in many applications. One of the most promising of the noncontact transducers is the electromagnetic acoustic transducer (EMAT). In general, an EMAT consists of a coil of wire which is positioned within a static magnetic field near the surface of a conducting material. When an RF current is applied to the coil, eddy currents are induced in the material. Lorentz forces are exerted on the eddy currents as a result of the magnetic field and are transmitted to the lattice structure of the material to generate an ultrasonic wave. A reduction in inspection time, an ability to operate in remote and inaccessible locations, and a reduction in transducer wear are all significant economic advantages which are offered by an EMAT-based nondestructive testing system.

EMATs may be fabricated with a number of different coil and magnet configurations to suit the requirements of a particular application. U.S. Pat. Nos. 3,850,028; 4,048,847; 4,080,836; 4,092,868; 4,104,922; 4,127,035; 4,184,374; 4,218,924; 4,232,557; and 4,248,092, for example, illustrate the variety of approaches which are available. While EMATs have thus been utilized in many nondestructive testing situations, the problem of exciting a broadband ultrasonic signal has presented a significant limitation in the past, since the narrowband operation traditionally employed limits resolution and consequently either restricts the operation of EMATs to parts of very simple geometry or requires extensive signal processing to separate flaw information from boundary information.

Early experiments showed that broadband operation could be achieved with relative ease at frequencies of a few MHz. At higher frequencies, however, broadband transduction becomes considerably more difficult because the inductance of the EMAT coil limits the rise time of the exciting current pulse. Thus, a new approach which would render an EMAT capable of efficiently generating and detecting ultrasonic wave energy over a wide range of frequencies would satisfy a long felt need in this area of technology.

SUMMARY OF THE INVENTION

It is a general objective of this invention to provide an improved broadband electromagnetic acoustic transduction technique.

The broadband electromagnetic acoustic transducer of this invention generally includes a source of magnetic flux for establishing a static magnetic field in an electrically conductive object. An electrical conductor is included for inducing eddy currents in the object when an alternating current is applied to the conductor. The magnetic field and the conductor are oriented so that the vector product of the magnetic field and the eddy currents produces an instantaneous force field in the object which is periodically alternately directed with a logarithmic periodicity.

In a first more particular embodiment, the transducer includes a plurality of alternately oriented magnets aligned along a propagation direction to establish a static magnetic field which is periodically alternately oriented such that the ratio of adjacent periods of the field is constant. An electrical conductor is included for inducing eddy currents in the object when an alternating current is applied to the conductor, the magnets and the conductor being oriented so that the vector product of the magnetic field and the eddy currents produces an instantaneous force field in the object which is periodically alternately directed with a logarithmic periodicity.

In a more particular embodiment, the transducer includes a source of magnetic flux for establishing a static magnetic field in the object and a serpentine electrical conductor for inducing eddy currents in the object when an alternating current is applied to the conductor. The conductor includes a plurality of periodically alternately oriented parallel elements which are perpendicular to a propagation direction, so that the ratio of adjacent periods is constant.

In a third more particular embodiment, the transducer includes a first plurality of alternately oriented magnets aligned along a propagation direction and a second plurality of alternately oriented magnets aligned along the propagation direction and adjacent to the first plurality so that adjacent magnets in the first and second pluralities are alternately oriented. These magnets establish a periodic alternately oriented static magnetic field so that the ratio of adjacent periods of the field in the propagation direction is constant. An electrical conductor is included for inducing eddy currents in the object when an alternating current is applied to the conductor, this conductor being made up of a first conducting element which extends under the first plurality of magnets, a second conducting element which extends under the second plurality of magnets, and a connecting conducting element which links the first and second conducting elements, the magnets and the conductor being so oriented that the vector product of the magnetic field and the eddy currents produces an instantaneous force field in the object which is periodically alternately directed with a logarithmic periodicity.

The invention also encompasses a method of generating a broadband acoustic wave in an electrically conductive object. The method includes the steps of providing a source of magnetic flux to establish a static magnetic field in the object and providing an electrical conductor to induce eddy currents in the objects when an alternating current is applied to the conductor. The source of magnetic flux and the conductor are so oriented that the vector product of the magnetic field and the eddy currents produces an instantaneous force field in the object which is periodically alternately directed with a logarithmic periodicity.

These examples summarize some of the more important features of this invention. There are, of course, additional details involved in the invention, which are further described below and which are included within the subject matter of the appended claims.

BRIEF DESCRIPTION OF THE DRAWINGS

Additional objectives, features, and advantages of the present invention will be evident from the description below of the preferred embodiments and the accompanying drawings, wherein the same numerals are used to refer to like elements throughout all the figures. In the drawings:

FIGS. 4-6 are perspective views of several other periodic permanent magnet EMATs embodying the invention.

DESCRIPTION OF THE PREFERRED EMBODIMENTS

Figure 1:
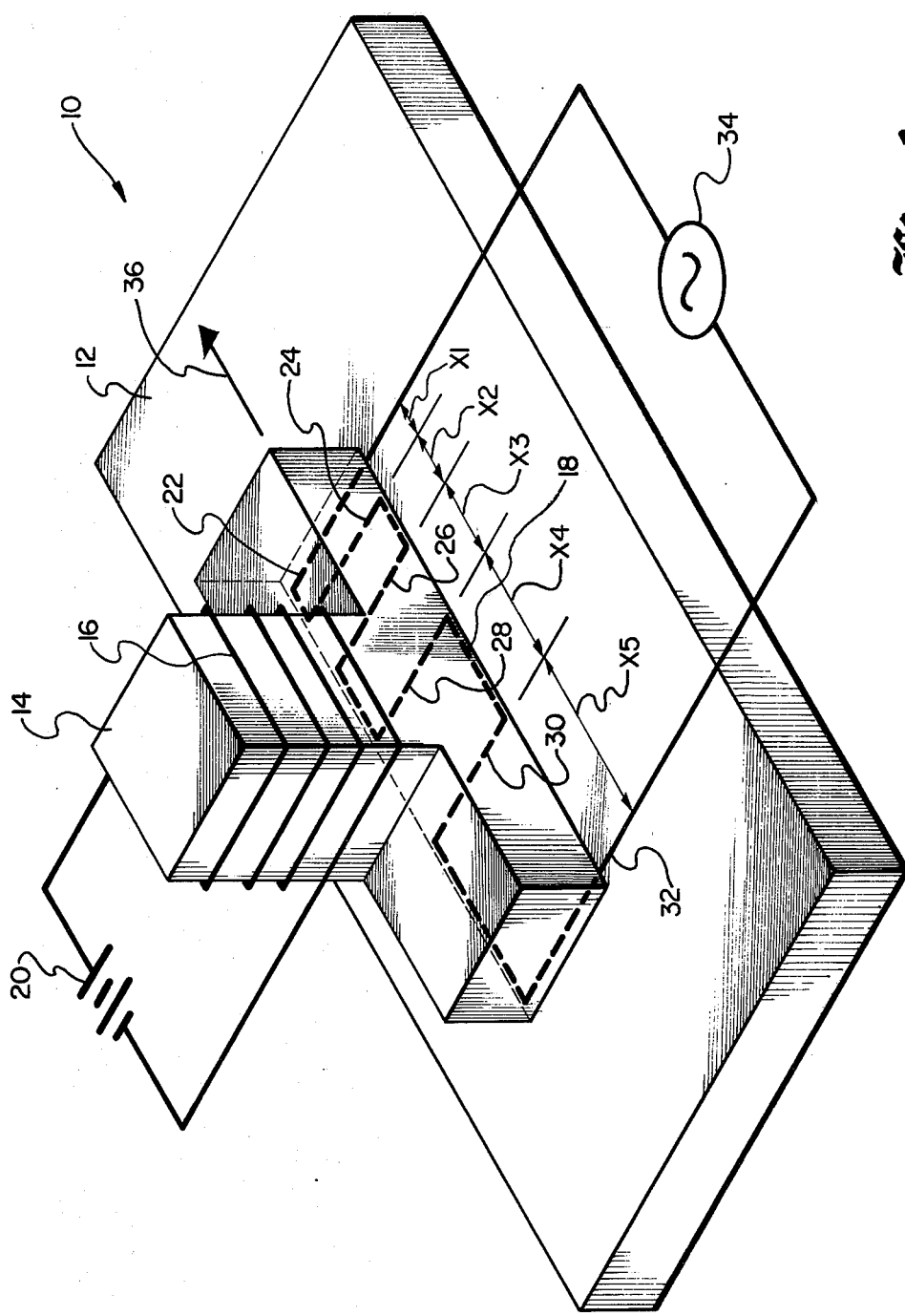
FIG. 1 illustrates one preferred embodiment of a broadband electromagnetic acoustic transducer constructed according to the present invention, shown in perspective view.

FIG. 1 provides a perspective view of a broadband electromagnetic acoustic transducer (EMAT) constructed according to the present invention.

The transducer 10, which is designed for the generation or detection of an ultrasonic wave in an electrically conductive object 12, includes an electromagnet, consisting of a core 14 and a coil 16, and a serpentine electrical conductor 18.

When the coil 16 is energized by connection to a source of DC power 20, the magnet provides a source of magnetic flux to establish a static magnetic field in the object. The serpentine conductor includes a number of periodically alternately oriented parallel elements 22, 24, 26, 28, 30 and 32. When an alternating current source 34 is applied to the conductor 18, these elements will induce eddy currents in the object 12.

It is an outstanding feature of this invention to provide an improved EMAT which demonstrates an enhanced wideband response in both the generation and the detection of ultrasonic waves. This improvement is achieved in the EMAT 10 of FIG. 1 by spacing the parallel elements 24-32 so that the ratio of adjacent periods (i.e., $x_{n+1}/x_n$) is constant. With the magnetic field oriented perpendicular to the surface of the object 12 and the elements 24-32 perpendicular to the magnetic field, the vector product of the magnetic field and the induced eddy currents will produce an instantaneous force field in the object 12 which is periodically alternately directed with a logarithmic periodicity. When this spatially periodic force field is repeatedly reversed in direction because of the alternating current source 32, an ultrasonic wave will be generated in the object 12 and will propagate in the direction indicated by the arrow 36.

As will be appreciated by those skilled in the art, the transducer 10 may also be used to detect an ultrasonic wave in the object 12 by a reciprocal process, whereby the detected wave induces an AC signal in the serpentine conductor 18.

The broad frequency capabilities of an EMAT built in accordance with this invention are achieved by incorporating "log-periodic" spacing in the EMAT. This technique is related to the design of a broadband radio frequency antenna. Perhaps the most successful broadband antenna is the log-periodic dipole antenna, which was introduced in 1955 by DuHamel and Isbell. This type of antenna consists of a series of dipoles arranged in a plane and connected to a transmission line. In the direction away from the terminals the dipoles are arranged in the order of increasing length with the ratio of lengths of adjacent elements having a constant value, usually between 0.75 and 0.9. In operation, only a few elements, the ones close to resonance, are excited. These elements comprise the active region. As the frequency of operaton is increased, the active region shifts from the rear of the antenna to the forward, terminal end. This log-periodic concept has proven useful in designing a large class of broadband antennas with bandwidths of 10:1 and higher.

Log-periodic RF antenna design techniques may be analogized to EMAT design. The analogy involves resolving a wire pair with associated biasing magnets to a dipole RF antennna. The wire pair-magnet arrangement develops a shear force in a conducting sample. By adding more magnets (i.e., more dipoles in the antenna analog) an end fire phased array type EMAT may be constructed. To obtain a broadband response from the end fire type RF antenna, the antenna elements are spaced logarithmically, i.e., such that the ratio of adjacent spacings is constant for all the elements. By adjusting the spacing of the EMAT magnets (or meander coil) in a similar fashion a broadband EMAT may be fabricated.

The broadband capabilities provided an EMAT by this invention should be useful in many applications. One of the most attractive features of this invention, for example, is the capability to implement pulse compression techniques. Pulse compression was developed as a means for increasing radar resolution and effective power. Ideally, it is most desirable for a radar receiver to receive a very narrow, high power pulse—narrow enough to pinpoint a target and powerful enough to stand out above a noisy background. A radar transmitter, however, is better suited to transmit a wide pulse with relatively low power. Pulse compression techniques allow both the transmitting and receiving modes to be idealized by transmitting a sequence of pulses of different frequencies at different times. When these pulses return to the receiver after reflection, they are first processed through a dispersive delay line which delays signals of different frequencies by different amounts. The pulses then arrive at the receiver simultaneously, their amplitudes add, and the receiver sees a single, large amplitude, narrow pulse.

The pulse compression technique can similarly be used with the EMAT of the present invention to achieve an ultrasonic signal which is narrow in width and high in power. The application of pulse compression to an ultrasonic flaw detection system can be analyzed by considering the transfer function approach. In this approach, a flaw is characterized by its effect on the transfer function, which is defined as the output of the system divided by the input. Since the best wave shape for an acoustic flaw interrogation signal is the impulse function, the problem is to generate an acoustic impulse in the object being evaluated.

The broadband EMAT of the present invention offers a solution to this problem, since it not only is useful over a wide range of frequencies, but is also characteristically phase dispersive. Consequently, if the electrical signal applied to energize the EMAT is in the form of an impulse, the EMAT will respond by generating a "chirped" acoustic wave, i.e., an acoustic signal whose wavelength is graduated from the highest frequency passed by the transducer to the lowest frequency passed by the transducer. If the broadband EMAT is considered to be a filter, matched filter theory then states that if the waveform output of the EMAT is reversed in time (i.e., the conjugate of the output) and used to drive the EMAT, the inverse result will obtain. In other words, by driving a broadband EMAT with an electrical input which is the conjugate of the characteristic chirped output for that EMAT, the EMAT may be made to generate an acoustic impulse for flaw interrogation.

Flaw detection using acoustic pulse compression techniques is thus made feasible by the broadband EMAT of the present invention. Furthermore, because of the inherent dispersive quality of the EMAT output, this acoustic pulse compression can be realized without the need for a delay line, as is required in radar pulse compression systems. Using this technique, a relatively low amount of average power in an input electrical signal may be compressed by the broadband EMAT into an acoustic impulse of short duration and very high power. The relatively large quantity of energy which can thus be introduced into a test object in impulse form can be used to resolve structural details on a smaller scale than has heretofore been practical.

Figure 2:
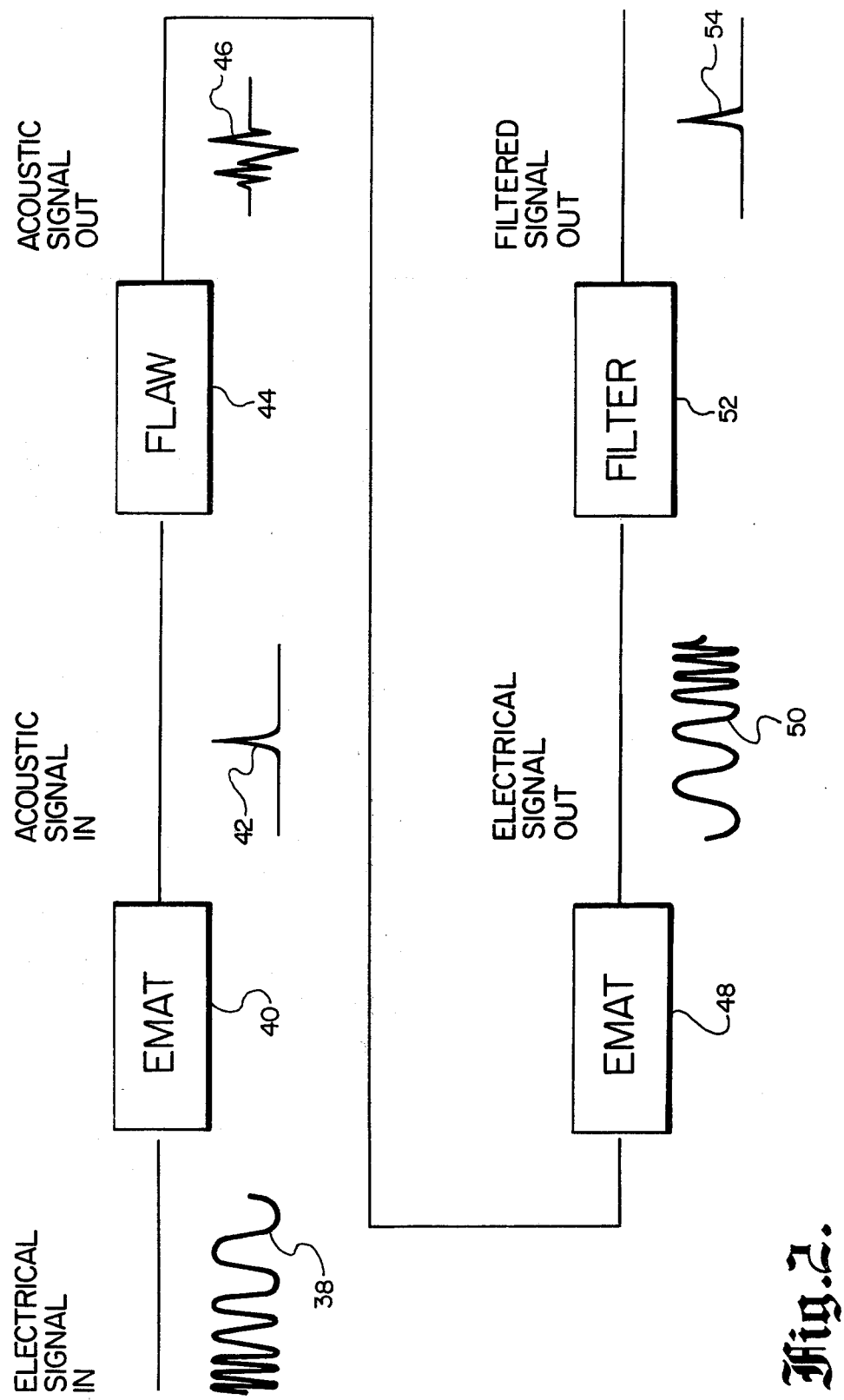
FIG. 2 is a schematic representation of an ultrasonic pulse compression flaw detection system.

This technique is illustrated in FIG. 2, which is a schematic representation of an ultrasonic pulse compression flaw detection system. A chirped electrical signal 38 is applied to energize the broadband EMAT 40, which is built according to the present invention. The EMAT 40 responds by generating an acoustic impulse signal 42 which is directed toward a flaw 44.

In addition to improving the characteristics of the input acoustic signal, pulse compression can also be used to enhance the analysis of the acoustic signal which is received after interrogation of a flaw. Where an acoustic impulse is injected into an object, the electrical output from a broadband EMAT detecting this signal, in the absence of a flaw, will be the chirped conjugate wave. The ideal output to facilitate signal processing, however, would be an impulse. Thus, analysis of the acoustic output can be facilitated by applying the electrical output of the detecting EMAT to a matched filter which will convert the conjugate signal into an electrical impulse, thereby compressing the power of the conjugate wave. The transfer function of any flaw which interacts with the acoustic signal will then be recognizable as a deviation from the ideal impulse function in the electrical output.

Thus, in FIG. 2 the flaw 44 interacts with the acoustic impulse signal 42, producing a complex acoustic output signal 46. This signal is detected by a second broadband EMAT 48 which, in the absence of the flaw-induced perturbations, would produce an output electrical signal 50 which is the reverse of the input signal 38. By adding an appropriate filter 52 to the system, the output signal in the absence of a flaw can be the impulse signal 54. The flaw can then be analyzed in terms of its effect on the output impulse signal.

Figure 3:
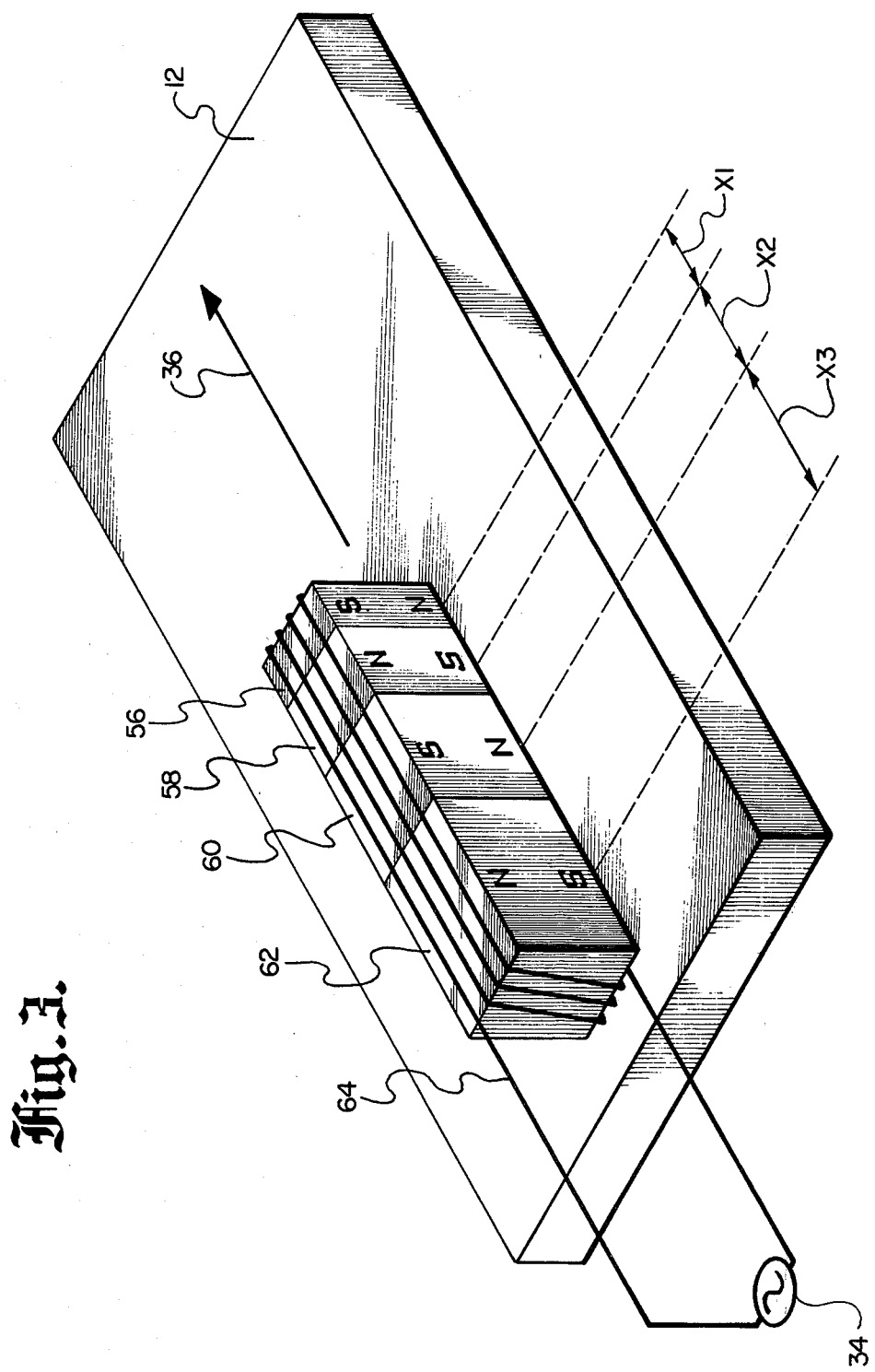
FIG. 3 is a perspective view of a periodic permanent magnet broadband EMAT.
Figure 4:
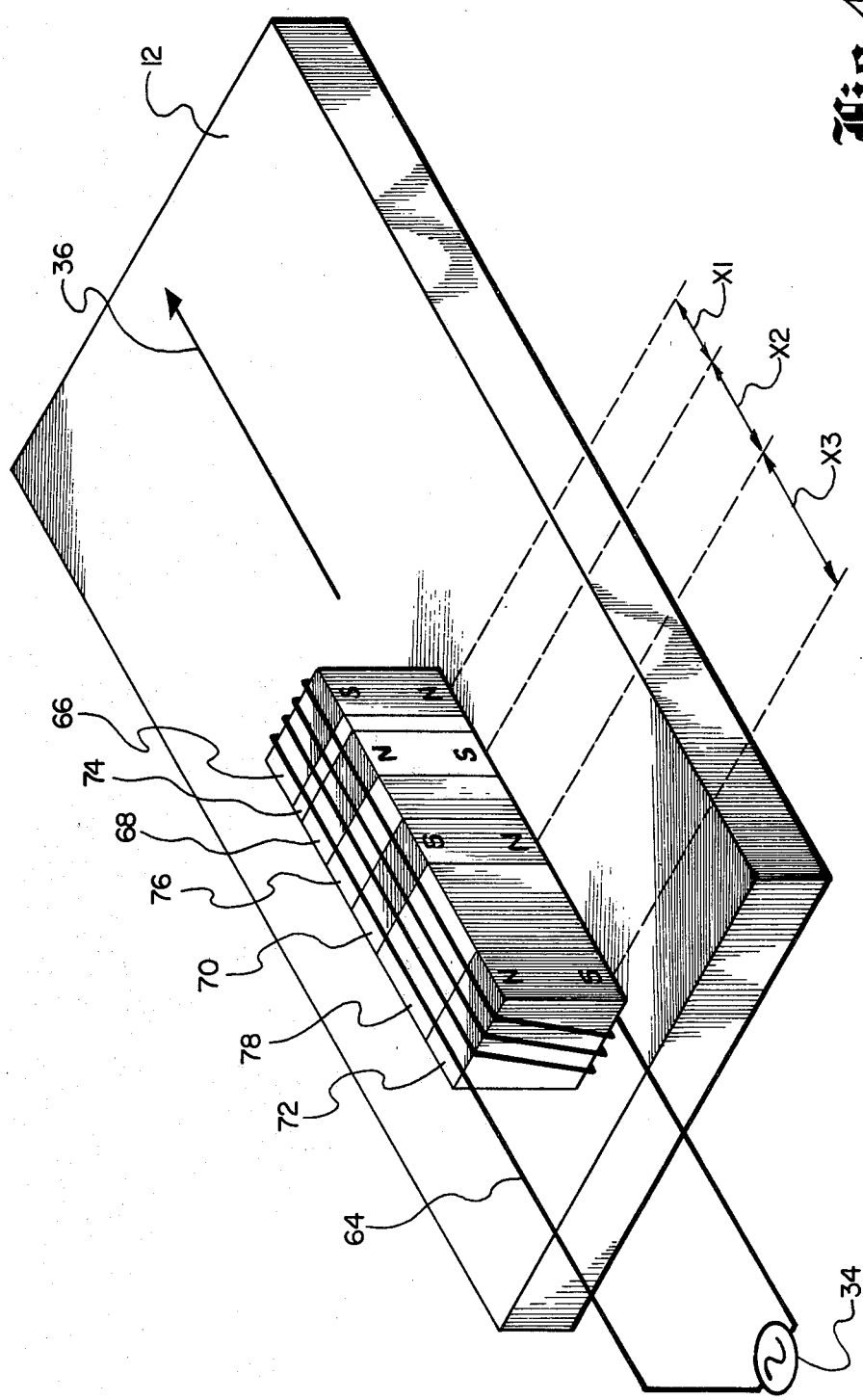

Another embodiment of the invention is illustrated in a perspective view in FIG. 3, with a number of alternately oriented magnets 56, 58, 60, and 62 oriented along a wave propagation direction, indicated by the arrow 36, so as to establish a static magnetic field which is periodically alternately oriented, with the ratio of adjacent periods of the fields being constant, i.e., $x_3/x_2 = x_2/x_1$. An electrical conductor is provided in the form of a wire coil 64 wound around the magnets such that the axis of the coil is perpendicular to the propagation direction and connected to a source 34 of alternating current. As in the embodiment of FIG. 1, this magnet and coil configuration is oriented so that the vector product of the magnetic field and the eddy currents induced by the coil produces an instantaneous force field in the object 12 which is periodically alternately directed with a logarithmic periodicity. With the magnetic and coil configuration of FIG. 3, horizontally polarized shear (SH) waves will be produced and will propagate in the direction of the arrow 36. An alternative technique for achieving the logarithmic periodicity featured in this invention is illustrated in FIG. 4. There, equally sized magnets 66, 68, 70, and 72 are spaced logarithmically by the insertion of appropriately sized spacers 74, 76, and 78 between the magnets.

Figure 5:
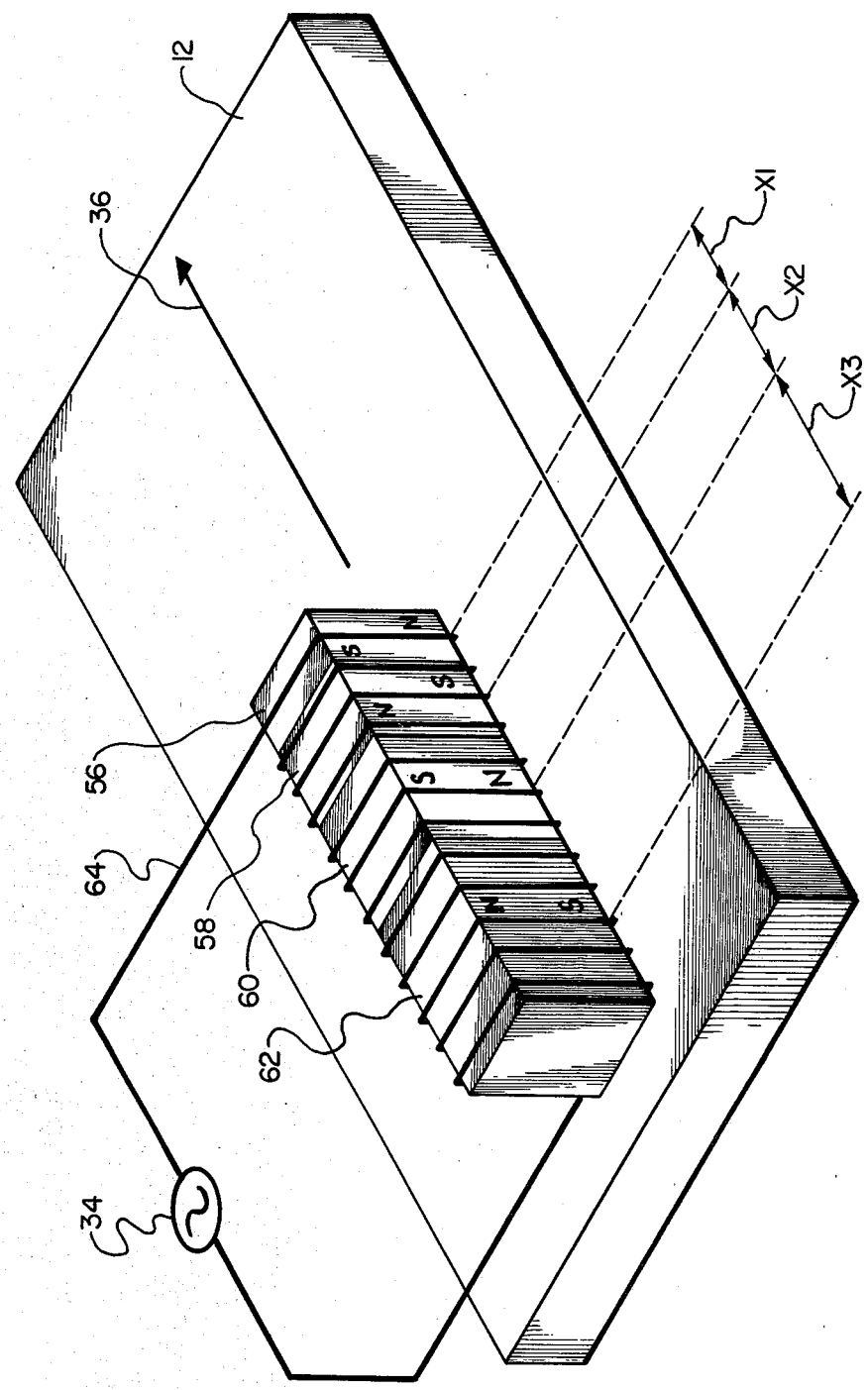

An embodiment similar to that of FIG. 3, but adapted to generate vertically polrized shear (SV) waves, is illustrated, again in perspective view, in FIG. 5. The magnet structure of this transducer is the same as that of FIG. 3, but the coil 64 is wound around the magnets so that the axis of the coil is parallel to the propagation direction, indicated by the arrow 36.

FIG. 6 illustrates yet another embodiment of the invention. There, a first row of alternately oriented magnets 80, 82, 84, and 86 is aligned parallel to the propagation direction indicated by the arrow 36, and a second row of alternately oriented magnets 88, 90, 92, and 94 is aligned parallel to the propagation direction and adjacent to the first row such that adjacent magnets in the first and second rows are alternately oriented. The two rows thus establish a periodic alternately oriented static magnetic field such that the ratio of adjacent periods $(x_{n+1}/x_n)$ of the field in the propagation direction (indicated by the arrow 36) is constant. The electrical conductor provided in this embodiment is a flat conductor which may be fabricated with printed circuit techniques. The conductor includes a first conducting element 96 which extends under the first row of magnets and a second conducting element 98 extending under the second row, with a linking element 100 connecting the first and second elements so that an AC source 34 can be applied to the conductor.

With this orientation of the magnets and the conductor, the vector product of the magnetic field and the eddy currents induced by the conductor will produce the desired logarithmically periodic force field to generate an ultrasonic wave in the object 12.

Although some typical embodiments of the present invention have been illustrated and discussed above, modifications and additional embodiments of the invention will undoubtedly be apparent to those skilled in the art. Various changes, for example, may be made in the configurations, sizes, and arrangements of the components of the invention without departing from the scope of the invention. Furthermore, equivalent elements maybe substituted for those illustrated and described herein, parts or connections might be reversed or otherwise interchanged, and certain features of the invention might be utilized independently of the use of other features. Consequently, the examples presented herein, which are provided to teach those skilled in the art how to construct the apparatus and perform the method of this invention, should be considered as illustrative only and not inclusive, the appended claims being more indicative of the full scope of the invention.

What is claimed is:

1. A broadband electromagnetic acoustic transducer for use with an electrically conductive object, comprising:
   a source of magnetic flux for establishing a static magnetic field in said object and
   an electrical conductor for inducing eddy currents in said object when an alternating current is applied to said conductor,
   said magnetic field and said conductor being so oriented that the vector product of said magnetic field and said eddy currents produces an instantaneous force field in said object, said force field being periodically alternately directed with a logarithmic periodicity such that the ratio of adjacent alternating periods within said force field is constant.

2. The transducer claim 1, wherein the smallest period of said logarithmic periodicity corresponds to the shortest wavelength acoustic wave to which said transducer is to respond and the largest period of said logarithmic periodicity corresponds to the longest wavelength acoustic wave to which said transducer is to respond.

3. The transducer of claim 1, wherein
   said source of magnetic flux further comprises a first plurality of alternately oriented magnets aligned along a propagation direction and a second plurality of alternately oriented magnets aligned along said propagation direction and adjacent to said first plurality such that adjacent magnets in said first and second pluralities are alternately oriented; and
   wherein said conductor further comprises a first conducting element extending under said first plurality of magnets parallel to said propagation direction, a second conducting element extending under said second plurality of magnets parallel to said propagation direction, and a connecting conducting element linking said first and second conducting elements at an end of said transducer.

4. The transducer of claim 1, wherein said conductor is periodically alternately oriented such that the ratio of adjacent periods of said conductor is constant.

5. The transducer of claim 4, wherein said conductor further comprises a serpentine conductor with a plurality of parallel elements perpendicular to a propagation direction, the ratio of adjacent spacings between said elements being constant.

6. The transducer of claim 1, wherein said magnetic field is periodically alternately oriented such that the ratio of adjacent periods of said field is constant.

7. The transducer of claim 6, wherein said source of magnetic flux further comprises a plurality of alternately oriented magnets aligned along a propagation direction.

8. The transducer of claim 7, wherein said conductor further comprises a coil encircling said plurality of magnets.

9. The transducer of claim 8, wherein the axis of said coil is parallel to said propagation direction.

10. The transducer of claim 8, wherein the axis of said coil is perpendicular to said propagation direction.

11. A broadband electromagnetic acoustic transducer for use with an electrically conductive object, comprising:
    a plurality of alternately oriented magnets aligned along a propagation direction to establish a static magnetic field which is periodically alternately oriented such that the ratio of adjacent periods of said field is constant; and
    an electrical conductor for inducing eddy currents in said object when an alternating current is applied to said conductor,
    said magnets and said conductor being so oriented that the vector product of said magnetic field and said eddy currents produces an instantaneous force field in said object, said force field being periodically alternately directed with a logarithmic periodicity such that the ratio of adjacent alternating periods within said force field is constant.

12. A broadband electromagnetic acoustic transducer for use with an electrically conductive object, comprising:
    a source of magnetic flux for establishing a static magnetic field in said object; and
    a serpentine electrical conductor for inducing eddy currents in said object when an alternating current is applied to said conductor, the conductor including a plurality of periodically alternately oriented parallel elements perpendicular to a propagation direction such that the ratio of adjacent periods is constant,
    said magnetic field and said conductor being so oriented that the vector product of said magnetic field and said eddy currents produces an instantaneous force field in said object, said force field being periodically alternately directed with a logarithmic periodicity such that the ratio of adjacent alternating periods within said force field is constant.

13. A broadband electromagnetic acoustic transducer for use with an electrically conductive object, comprising:
    a first plurality of alternately oriented magnets aligned along a propagation direction;
    a second plurality of alternately oriented magnets aligned along said propagation direction and adjacent to said first plurality such that adjacent magnets in said first and second pluralities are alternately oriented, said magnets establishing a periodic alternately oriented static magnetic field such that the ratio of adjacent periods of said field in said propagation direction is constant; and an electrical conductor for inducing eddy currents in said object when an alternating current is applied to said conductor, said conductor including:
- a first conducting element extending under said first plurality of magnets,
- a second conducting element extending under said second plurality of magnets, and
- a connecting conducting element linking said first and second conducting elements, said magnets and said conductor being so oriented that the vector product of said magnetic field and said eddy currents produces an instantaneous force field in said object, said force field being periodically alternately directed with a logarithmic periodicity such that the ratio of adjacent alternating periods within said force field is constant.

14. A method of generating a broadband acoustic wave in an electrically conductive object, comprising the steps of:
providing a source of magnetic flux to establish a static magnetic field in the object;
providing an electrical conductor to induce eddy currents in the object when an alternating current is applied to the conductor; and
orienting the source of magnetic flux and the conductor so that the vector product of the magnetic field and the eddy currents produces an instantaneous force field in the object, the force field being periodically alternately directed with a logarithmic periodicity such that the ratio of adjacent alternating periods within the force field is constant.

15. The method of claim 14, wherein the step of providing a source of magnetic flux further comprises providing a source of magnetic flux to establish a static magnetic field in the object which is periodically alternately oriented such that the ratio of adjacent periods of the field is constant.

16. The method of claim 14, wherein the step of providing an electrical conductor further comprises providing an electrical conductor which is periodically alternately oriented such that the ratio of adjacent periods of the conductor is constant.

17. The method of claim 15 or 16, further comprising the step of applying an alternating current to the conductor which is swept in frequency such that the broadband acoustic wave is generated in the form of an impulse.

* * * * *